(12) United States Patent
Sinha et al.

(10) Patent No.: US 7,537,889 B2
(45) Date of Patent: May 26, 2009

(54) **ASSAY FOR QUANTITATION OF HUMAN DNA USING *ALU* ELEMENTS**

(75) Inventors: Sudhir K. Sinha, Metairie, LA (US); Jerilyn A. Walker, Breaux Bridge, LA (US); Mark A. Batzer, Mandeville, LA (US)

(73) Assignees: Life Genetics Lab, LLC., New Orleans, LA (US); Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 455 days.

(21) Appl. No.: 10/673,575

(22) Filed: Sep. 30, 2003

(65) Prior Publication Data

US 2005/0069902 A1    Mar. 31, 2005

(51) Int. Cl.
*C12Q 1/68* (2006.01)
(52) U.S. Cl. .......................................................... 435/6
(58) Field of Classification Search ..................... 435/6, 435/91.2
See application file for complete search history.

(56) References Cited

U.S. PATENT DOCUMENTS 4,683,202 A    7/1987    Mullis

OTHER PUBLICATIONS

Palmirotta et al. ("Origin and Gender Determination of Dried Blood on a Statue of the Virgin Mary" Journal of Forensic Science. Mar. 1998. (43) 2, pp. 431-434).*
Carroll et al. ("Large-scale Analysis of the Alu Ya5 and Yb8 Subfamilies and their Contribution to Human Genomic Diversity" Journal of Molecular Biology. 2001. 311, pp. 17-40).*
Hoglund et al. ("Isolation and characterization of radiation hybrids for human chromosome 12" Cytogenetic Cell Genetics. 1995. 69, pp. 240-245).*
Jurka ("A new subfamily of recently retroposed human Alu repeats" Nucleic Acids Research. 1993. vol. 21. No. 9, p. 2252).*
Batzer et al. ("Standardized Nomenclature for Alu Repeats" Journal of Molecular Evolution. 1996. 42, pp. 3-6).*
Gelmini et al. ("Quantitative polymerase chain reaction-based homogeneous assay with fluorogenic probes to measure c-erbB-2 oncogene amplification" Clinical Chemistry. 1997. 43:5, pp. 752-758).*

Tagle et al. ("An optimized Alu-PCR primer pair for human-specific amplification of YACs and somatic cell hybrids" Humna Molecular Genetics. 1992. vol. 1, No. 2: pp. 121-122).*
Keller et al. ("Molecular evolution of the CMT1A-REP region: a human- and chimpanzee-specific repeat. Mol Biol Evol. Aug. 1999;16(8):1019-26").*
Brooks-Wilson et al. (Rapid cloning and characterization of new chromosome 10 DNA markers by Alu element-mediated PCR. Genomics. Aug. 1990;7(4):614-20).*
Buck et al. ("Design Strategies and Performance of Custom DNA Sequencing Primers") BioTechniques. Sep. 1999. 27: pp. 528-536.*
Batzer et al. "Standardized Nomenclature for Alu Repeats" Journal of Molecular Evolution. 1996. 42, pp. 3-6).*
Sifis et al. ("A more sensitive method for the quantitation of genomic DNA by Alu amplification. J Forensic Sci. May 2002;47(3):589-92").*
Fortina et al. ("Non-radioactive detection of the most common mutations in the cystic fibrosis transmembrane conductance regulator gene by multiplex allele-specific polymerase chain reaction" Hum Genet. Dec. 1992;90(4):375-8).*
Hedges et al., "*Mobile Element-Based Assay for Human Gender Determination*," Analytical Biochemistry 312, pp. 77-79, 2003.
Walker et al., "*Quantitative Intra-Short Interspersed Element PCR for Species-Specific DNA Identification*," Analytical Biochemistry 316, pp. 259-269, 2003.
Walker et al., "*Human DNA Quantitation Using Alu Element-Based Polymerase Chain Reaction*," Analytical Biochemistry 315, pp. 122-128, 2003.
Nicklas et al., "*Development of an Alu-Based, QSY 7-Labeled Primer PCR Method for Quantitation of Human DNA in Forensic Samples*," J Forensic Science vol. 48, No. 2, pp. 282-291, Mar. 2003.
Nicklas et al., "*Development of Alu-Based, Real-Time PCR Method for Quantitation of Human DNA in Forensic Sample*," J Forensic Science vol. 48, No. 5, pp. 936-944, Sep. 2003.
Kass et al., "*Inter-Alu Polymerase Chain Reaction: Advancements and Applications*", Analytical Biochemistry vol. 288, pp. 185-193,1995.

* cited by examiner

*Primary Examiner*—Kenneth R. Horlick
*Assistant Examiner*—Christopher M. Babic
(74) *Attorney, Agent, or Firm*—Robert E. Bushnell, Esq.

(57) ABSTRACT

An assay for determining presence of human DNA in a sample in which non-human DNA may also be present and for quantitating such human DNA. One embodiment uses intra-Alu based PCR and another uses inter-Alu based PCR. The assays are performed without unique, expensive equipment. The assays are based on detection of multiple-copy Alu elements recently integrated into the human genome that are largely absent from non-human primates and other mammals.

9 Claims, 7 Drawing Sheets

```
AluY    GGCCGGGCGCGGTGGCTCACGCCTGTAATCCCAGCACTTTGGGAGGCCGA    50
AluYb8  ..................................................    50
AluYd6  ..................................................    50

AluY    GGCGGGCGGATCACGAGGTCAGGAGATCGAGACCATCCTGGCTAACACGG    100
AluYb8  .......T......T..................................A..    100
AluYd6  ............................C-------------..          88

AluY    TGAAACCCCGTCTCTACTAAAAATACAAAAAATTAGCCGGGCGTGGTGGC    150
AluYb8  .............................................C......    150
AluYd6  .............................................CA.....    138

AluY    GGGCGCCTGTAGTCCCAGCTACTCGGGAGGCTGAGGCAGGAGAATGGCGT    200
AluYb8  ..................................................    200
AluYd6  ..................................................    188

AluY    GAACCCGGGAGGCGGAGCTTGCAGTGAGCCGAGATCGCGCCACTGCACTC    250
AluYb8  ..........A.........................T..........G..    250
AluYd6  ........A...................G...............A......    238

AluY    CA-------GCCTGGGCGACAGAGCGAGACTCCGTCTCAAAAAA    287
AluYb8  .GCAGTCCG...................................    294
AluYd6  .C-------...............AA..................    275
```

Figure 2

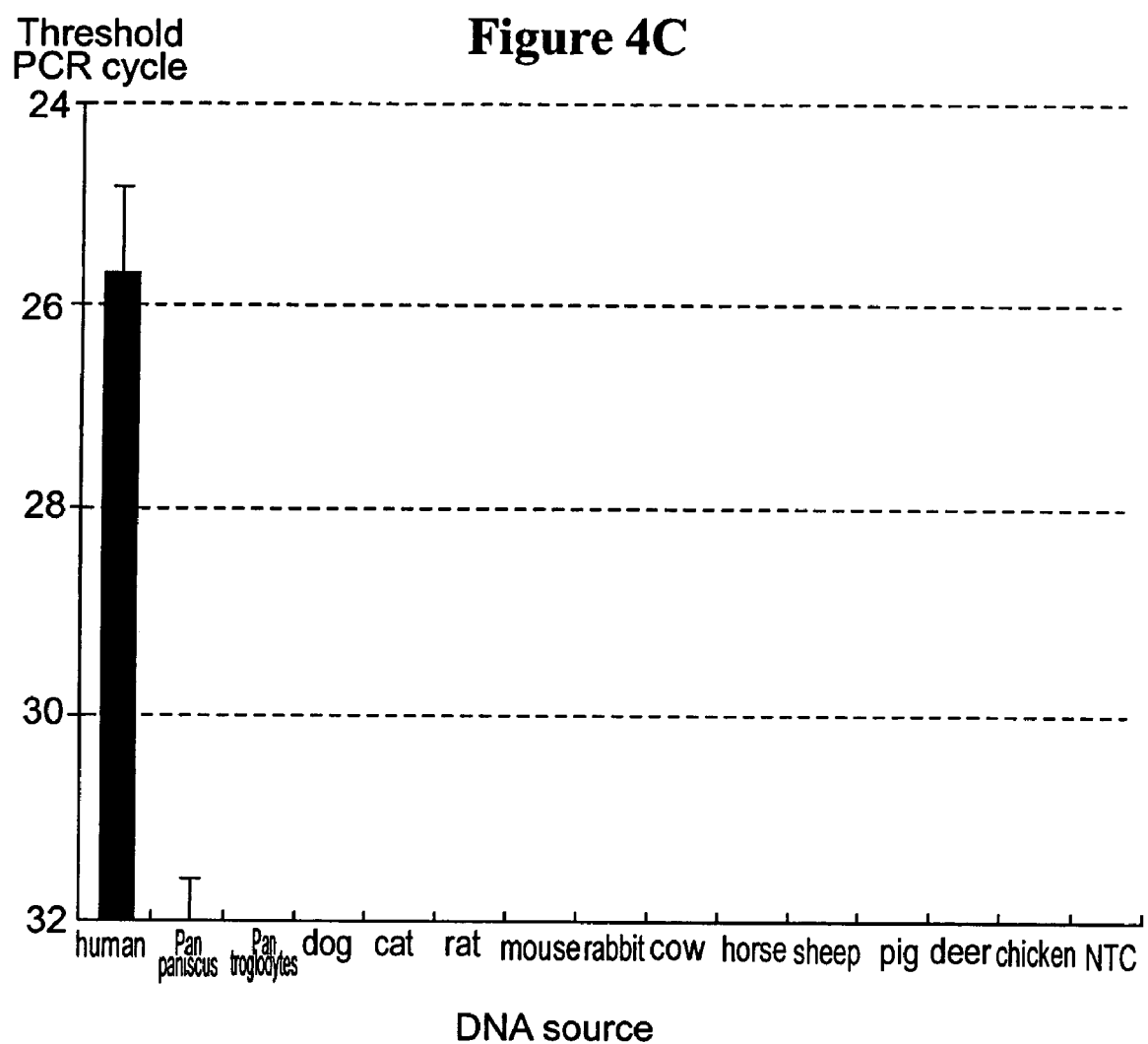

ASSAY FOR QUANTITATION OF HUMAN DNA USING *ALU* ELEMENTS

BACKGROUND OF THE INVENTION

1. Field of the Invention

The present invention concerns an assay for quantitating human DNA, particularly quantitating human DNA present in samples containing extraneous nonhuman DNA.

2. Description of the Related Art

The quantitative detection of bio-materials in mixed forensic samples has been approached using a variety of different systems. Early approaches to identify the origin of mixed sample components involved the use of high-performance liquid chromatography (HPLC) based methods. See H. F. Inoue et al., *Species Identification of Blood and Bloodstains by High-Performance Liquid Chromatography*, INT. J. LEGAL MED. 104:9-12 (1990). These methods have proven useful, although the detection limits using these approaches are restrictive. The detection of single copy nuclear DNA (Deoxyribonucleic acid) sequences has also been useful in this regard, but is limited as a result of their single copy. Polymerase chain reaction (PCR) based analysis of mitochondrial DNA sequences has also been used in the analysis of complex DNA samples. The advantage of mitochondrial based DNA analyses derives from the fact that there are many mitochondria per cell, and many mitochondrial DNA molecules within each mitochondria making mitochondrial DNA a naturally amplified source of genetic variation. See R. L. Cann et al., *Mitochondrial DNA and Human Evolution*, NATURE 325:31-36 (1987). However, a significant proportion of human forensic casework involves the analysis of nuclear loci. See R. Chakrabarty et al., *The Utility of Short Tandem Repeat Loci beyond Human Identification: Implications for Development of New DNA Typing Systems*, ELECTROPHORESIS 20:1682-1696 (1999), making the identification and quantitation of human nuclear DNA a paramount issue.

Commercially available products for human DNA quantitation include the Quantiblot® (Applied Biosystems, Inc.) and the AluQuant® (Promega Corporation) systems. The Quantiblot® system is based on the hybridization of a biotinylated oligonucleotide probe to extracted DNA, followed by visual comparison of the colorimetric or chemiluminescent sample results to the DNA standards. The AluQuant® system utilizes a luciferase reaction that results in light output suitable for interpretation with a luminometer. M. N. Mandrekar et al., *Development of a Human DNA Quantitation System*, CROAT. MED. J. 42: 336-339 (2001).

These systems can become quite costly, particularly if a luminometer needs to be purchased. The Quantiblot® and AluQuant® systems also detect non-human primate DNA, as well as human DNA, and the detection limit for each of these systems is approximately 0.1 ng (nanogram). These proprietary systems use technology that is not known to the public, because it is apparently being maintained as a trade secret. Although Promega uses the trademark "AluQuant®," it is not known whether the technology actually uses Alu elements, and there is considerable doubt in this regard because the system detects non-human DNA, which is not consistent with the best Alu-based technology.

The use of Alu PCR amplification has been proposed as a more sensitive method for the quantitation of genomic DNA compared to typical blot-based procedures currently used in most forensic laboratories. See M. E. Sifis et al., *A More Sensitive Method for the Quantitation of Genomic DNA by Alu Amplification*, J. FORENSIC SCI. 47:589-592 (2002). Note that the term "AluQuant" is a trademark of Promega Corporation and the AluQuant® system may not necessarily be based on Alu mobile elements, per se.

Alu elements are transposable DNA elements which have amplified to a copy number of over 1 million elements throughout primate evolution, thus producing a series of subfamilies of Alu elements that appear to be of different genetic ages. The expansion of these elements throughout primate evolution has created several recently integrated "young" Alu subfamilies that are present in the human genome but are largely absent from non-human primates. M. A. Batzer and P. L. Deininger, *Alu Repeats and Human Genomic Diversity*, NAT. REV. GENET. 3:370-379 (2002). These human-specific subfamilies only have a fraction of the copy number compared to primate-specific elements, however, so that they are relatively less available for assay use.

Recently Sifits, et al., supra, reported a method whereby a fluorescently labeled oligonucleotide PCR primer pair was designed to amplify a generic Alu sequence within primate DNA. They reported that the assay had a sensitivity level of 100-2.5 pg of DNA, which is an improvement over other assays with detection limits of 100-150 pg. However, their assay did not distinguish human from non-human DNA in forensic samples that were contaminated with non-human DNA, which frequently occurs.

Therefore, a need exists for a sensitive assay capable of quantitating human DNA present in samples also containing extraneous non-human DNA.

SUMMARY OF THE INVENTION

Accordingly, it is an object of the present invention to provide a human DNA quantitation method.

It is an object of the present invention to provide a sensitive assay for quantitating human DNA present in samples also containing extraneous non-human DNA.

It is another object to provide a series of subfamily-specific Alu-based PCR assays.

In each case, the assay includes three basic steps. First, a DNA-containing sample to be analyzed is provided. Second, amplification (preferably PCR (polymerase chain reaction)) of predetermined genomic DNA sequences occurs. The sequences are located between adjacent Alu elements, and the sequences are selected from Alu subfamilies present only in the human genome. The second step results in an amplified DNA product. Third, the amplified DNA product is compared with a reference.

For simply determining whether or not human DNA is present in a DNA sample, inter-Alu and intra-Alu assays are described hereinbelow, including appropriate primers. Since the loci selected for amplification are associated with Alu insertions present only in the human genome (and absent from other primate or mammalian genomes), an amplified DNA product occurs only for DNA samples containing human DNA. Thus, the reference for comparison purposes is the original sample. The amplification of human template DNA in the process described hereinbelow is an exponential increase, but there is essentially no amplification of non-human DNA. The particular Alu subfamilies selected for purposes of the assay were the Yb8 and Yd6 subfamilies, because of their large characteristic diagnostic insertion or deletion. The kit for performing this method includes the primers, polymerase chain reaction reagents such as polymerase and buffers, and a reference for comparing the amplified multiple copies of the Alu element to quantitate the human DNA. The kit optionally further includes reagents for extracting and isolating DNA from the sample, reagents for detecting the human DNA on an agarose gel stained with ethidium bromide, fluorescent dye and/or SYBR® green PCR core agents. The primers used for the inter Alu PCR method include Alu 3-5' GATCGCGCCACTGCACTCC 3' (SEQ ID NO: 1) and Alu 5-5' GGATTACAGGCGTGAGC-CAC 3' (SEQ ID NO: 2). The primers used for the intra-Yb8-based PCR assay comprise 5' CGAGGCGGGTGGATCAT-GAGGT 3' (SEQ ID NO: 3) and 5' TCTGTCGCCCA GGCCGGACT 3' (SEQ ID NO: 4). The primers used for the intra-Y6b-based PCR preferably include 5' GAGATC-GAGACCACGGTGAAA 3' (SEQ ID NO: 5) and 5' TTTGAGACGGAGTCTCGTT 3' (SEQ ID NO: 6).

BRIEF DESCRIPTION OF DRAWINGS

A more complete appreciation of the invention, and many of the attendant advantages thereof, will be readily apparent as the same becomes better understood by reference to the following detailed description when considered in conjunction with the accompanying drawings in which like reference symbols indicate the same or similar components, wherein:

FIG. 2 shows sequence alignment of Alu families;

FIGS. 4A through 4C show background amplification using non-human DNA templates.

DETAILED DESCRIPTION OF THE PREFERRED EMBODIMENTS

Primer Design and PCR Amplification

Inter-Alu Primers

Figure 1:
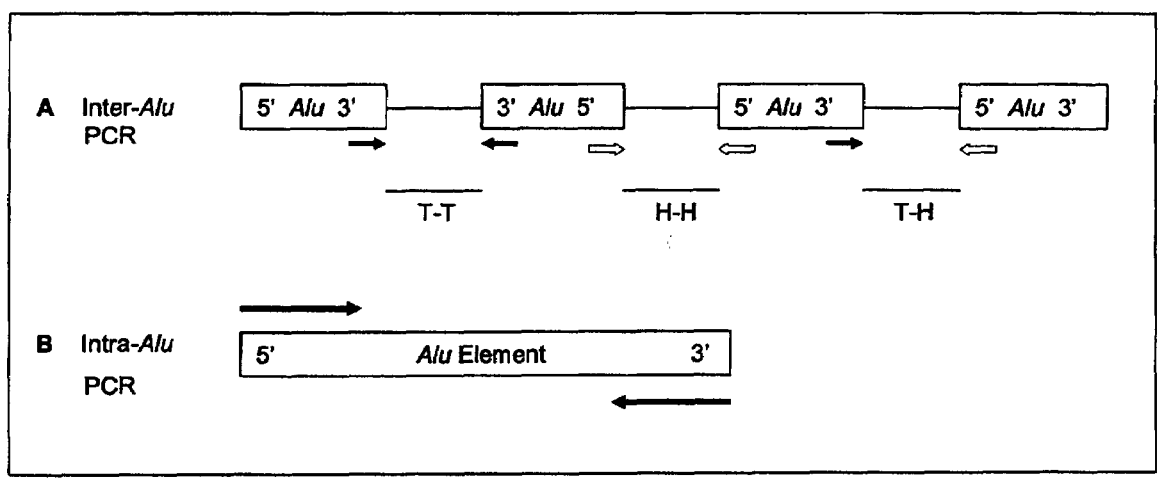
FIG. 1 is a schematic diagram showing inter-Alu and intra-Alu PCR.

Oligonucleotide primers selected for inter-Alu PCR are:

```
Alu 3-  5'GATCGCGCCACTGCACTCC 3'    (SEQ ID NO: 1)
and

Alu 5-  5'GGATTACAGGCGTGAGCCAC 3'.  (SEQ ID NO: 2)
```

Intra-Alu Primers

The Alu subfamily-specific intra-Yb8 primers selected are:

```
5'
CGAGGCGGGTGGATCATGAGGT 3'  (SEQ ID NO: 3)  (position
                                            48 to 69)
and 5' TCTGTCGCCCAGGCCGGACT 3' (SEQ ID NO: 4)  (position
                                            273 to
                                            254).
```

(The diagnostic bases are shown here in italics and underlined.)

The forward intra-Yd6 primer selected is:

5' GAGATCGAGACCAC/GGTGAAA 3' (SEQ ID NO: 5), which crosses the characteristic Yd subfamily deletion, marked by the slash. The reverse intra-Yd6 primer selected is:

5' TTTGAGACGGAGTCTCGTT 3' (SEQ ID NO: 6), which contains a Yd6 subfamily-specific diagnostic mutation at the penultimate base.

Intra-Alu oligonucleotide primers are designed using either Primer3 software (Whitehead Institute for Biomedical Research, Cambridge, Mass., USA) or Primer Express software (Applied Biosystems). The need to incorporate subfamily specific diagnostic mutations into the primer design, as well as the high intrinsic GC content of Alu repeats, made it challenging to identify oligonucleotide primers acceptable to the design software packages. Oligonucleotides were purchased from Sigma-Genosys, Inc. The SYBR® green PCR core reagent kit for quantitative PCR was purchased from Applied Biosystems, Inc.

PCR Reaction Conditions

PCR conditions were optimized for each assay with regard to annealing temperature and concentrations of $MgCl_2$ and oligonucleotide primers. PCR reactions were carried out in 50 µl (microliter) using 1× SYBR green buffer, 1 mM dNTPs and 1.25 units AmpliTaq Gold® DNA polymerase as recommended by the supplier. Inter-Alu PCR used 2 µM of each oligonucleotide primer and 3 mM $MgCl_2$. Each sample was subjected to an initial denaturation of 12 minutes at 95° C. to activate the AmpliTaq Gold®, followed by 40 amplification cycles of denaturation at 95° C. for 20 seconds, 56° C. to anneal for 1 minute, and 1 minute of extension at 72° C. Intra-Yb8 PCR used one µM of each oligonuclotide primer, 3 mM $MgCl_2$, an initial denaturation of 12 minutes at 95° C., followed by 40 amplification cycles of 95° C. for 15 seconds and 74° C. for 1 minute to anneal and extend. Intra-Yd6 PCR used 0.5 µM of each oligonuclotide primer, 5 mM $MgCl_2$, an initial denaturation of 12 minutes at 95° C., followed by 40 amplification cycles of 95° C. for 15 seconds and 61° C. for 1 minute to anneal and extend. Each reaction contained 49 µl of PCR master mix and 1 µl of DNA template. Quantitative PCR experiments were performed using an ABI Prism 7000 sequence detection system (Applied Biosystems, Inc.) or a Bio-Rad i-cycler iQ real-time PCR detection system.

Cell Lines and DNA Samples

The cell lines used to isolate DNA samples were HeLa (*Homo sapiens*), pygmy chimpanzee (*Pan paniscus*), and chimpanzee (*Pan troglodytes*) as described in M. A. Batzer, et al., *Standardized nomenclature for Alu repeats*, J. MOL. EVOL. 42:3-6 (1996). DNA from non-primate species was obtained by tissue and blood extraction using the Wizard Genomic DNA Purification kit (Promega) and samples provided by the Louisiana State University School of Veterinary Medicine. Human control DNA (HeLa) was serially diluted 10-fold in 10 mM Tris/0.1 mM EDTA (ethylenediaminetetraacetic acid) such that concentrations from 100 ng to 0.1 pg were evaluated in replicates of two to four each.

Data Analysis

Data from the replicate DNA standards were exported from ABI Prism 7000 SDS software® into a Microsoft® Excel spreadsheet where the mean value and standard deviation were calculated for each point on the standard curve. The negative control (no template—NT) was included in these calculations but was considerably lower than the last data point for inter-Alu and intra-Yd6 standard curves and therefore does not appear on those charts, but does appear on the intra-Yb8 chart. Using the Excel trendline option, a line of best fit was plotted with Y-error bars equal to one standard deviation. Data from the non-human DNA cross-hybridization/amplification experiments were exported to Excel in a similar manner and the mean and standard deviation were calculated for each of four replicates. The Excel chart wizard was used to construct bar graphs with Y-error bars equal to one standard deviation.

Resulting Assays

As a result of the foregoing techniques, several Alu element-based assays have been developed for the rapid identification, and quantitation of human DNA present in a sample mixed with non-human DNA. The assay approaches are respectively inter-Alu and intra-Alu PCR based methods (see FIG. 1) in conjunction with SYBR® green fluorescence detection (trademark of Molecular Probes, Inc.).

Referring to FIG. 1, a schematic representation of inter-Alu and intra-Alu PCR, the rectangles represent 5'-3' or 3'-5' orientation of Alu elements in the genome. During inter-Alu PCR the 5' primer (unshaded arrows) and the 3' primer (small black arrows) amplify genomic DNA sequences between adjacent Alu elements (dark lines) in any possible orientation, "tail-to-tail" (T-T), "head-to-head" (H-H), or "tail-to-head" (T-H). During intra-Alu PCR, primers are designed within the core body of the Alu element to amplify multiple copies of the element derived from locations dispersed throughout the genome.

Inter-Alu PCR was originally developed, see D. L. Nelson et al., *Alu polymerase chain reaction: a method for rapid isolation of human-specific sequences from complex DNA sources*, PROC. NAT'L ACAD. SCI. USA 86:6686-6690 (1989), to detect human DNA sequences in somatic cell hybrids. Oligonucleotide primers were designed, based upon the primate Alu consensus sequence and used to amplify unique human DNA sequences between adjacent Alu repeats in an effort to isolate large regions of human DNA without the laborious task of first creating a recombinant library from the somatic cell hybrids. Later, the technique was improved by primers, Alu 5'/3' which amplified human DNA sequences between adjacent Alu repeats, regardless of their orientation in the genome, and reportedly could generate PCR products detectable by ethidium bromide staining from as little as 0.001 ng of human genomic DNA. Inter-Alu PCR generates a complex pool of PCR amplicons of different sizes.

By contrast, intra-Alu PCR generates a homogeneous product composed entirely of repeat core unit DNA sequences characteristic of the element being amplified. This approach is similar in general concept to the primate Alu assay developed by Sifits et al, supra.

However, the assay of the present invention is instead based on the limited amplification of members of those young Alu subfamilies that are present in the human genome but are absent from non-human primate genomes. The subfamilies we selected for intra-Alu evaluation were Yb8 and Yd6 because of the large diagnostic insertion or deletion that is characteristic of these Alu families. The Yb8 subfamily consensus sequence contains eight individual diagnostic mutations different from the ancestral Alu Y subfamily, as well as a seven nucleotide insertion at position 253 (see FIG. 2). FIG. 2 illustrates sequence alignment of Alu subfamilies. The consensus sequence (SEQ ID NO: 7) for the Alu Y subfamily is shown at the top. The sequence (SEQ ID NO: 8) for Alu Yb8 subfamily is shown at the second line, and the sequence (SEQ ID NO: 9) for Yd6 subfamily is shown at the last line. The dots represent the same nucleotide as the Alu Y consensus sequence. Deletions are shown as dashes and mutations are shown as the correct base for each subsequent subfamily. Sequences of the subfamily specific intra-Alu oligonucleotide primers for amplification of the Alu core body sequence only are shown in bold font.

There are estimated 1852 Yb8 Alu elements in the human genome. M. L. Carroll, et al., *Large-scale analysis of the Alu Ya5 and Yb8 subfamilies and their contribution to human genomic diversity*, J. MOL. BIOL. 311:17-40 (2001) The recently reported Yd6 subfamily has six subfamily specific diagnostic mutations as well as a twelve nucleotide deletion starting at position 87 that defines the Yd lineage from the draft sequence of the human genome; and estimated 97 Yd6 Alu subfamily members are present in the human genome. See M. A. Batzer et al., *Standardized nomenclature for Alu repeats*, J. MOL. EVOL. 42:3-6 (1996).

The following examples illustrate execution of the inventors' assays, using several different test samples. Sample #1 is a human DNA sample without non-human DNA present. Sample #2 is a human DNA sample with pygmy chimpanzee (*Pan paniscus*), and common chimpanzee (*Pan troglodytes*) DNA also present. Sample #3 is a human DNA sample with other mammalian DNA also present (45% canine, 45% feline, and 10% human DNA).

EXAMPLE 1

Inter-Alu Assay of Human DNA

Sample #1 was prepared as follows. Approximately 1 μl of capillary blood from a male donor was washed twice in 500 μl of distilled water and mixed with a conventional reaction buffer for PCR. See, e.g., Chien et al., J. BACTER. 127:1550 (1976). The mixture was mixed with 100 μl of a known amplification buffer—10 mM Tris-HCl, pH 8.4 at 20° C., 1.5 mM MgCl2, 50 mM KCl, 2'-deoxyadenosine 5'-triphosphate (dATP), 2'-deoxycytidine 5'-triphosphate (dCTP), 2'-deoxyguanosine 5'-triphosphate (dGTP), 2'-deoxythymidine 5'-triphosphate (dTTP), 0.2 mM each, 1.2 mM each primer. A conventional PCR followed, using approximately 40 cycles over approximately 3 hours. The generation of PCR products or amplicons was directly monitored using a PCR machine with an optical detection unit (quantitative PCR machine). The amplification of human template DNA resulted in an exponential increase in the amount of product produced.

EXAMPLE 2

Inter-Alu Assay of Human/Primate DNA

Sample #2 was prepared as follows. Equal amount of human and chimpanzee DNA derived from tissue culture lines were mixed together and subjected to the same amplification protocol outlined above. Using this approach we were able to compare the amplification derived from a human template to that of a mixed template and that of a sample that contained only non-human primate DNA (pygmy or common chimpanzee). The assay resulted in the exponential amplification of DNA in samples that contained human DNA templates and essentially no amplification in samples that only contained non-human primate DNA.

EXAMPLE 3

Inter-Alu Assay of Human/Mammal DNA

In this example DNA derived from cell lines or from peripheral lymphocytes derived from a number of different mammals was subjected to inter-Alu PCR and optical detection. Since Alu repeats are contained only within members of the primate order and recently integrated Alu elements are found only within the human genome, little or no amplification was to be expected in the test samples that contained the DNA of other animals as templates. As was to be expected, essentially no amplification of PCR products was detected in these samples. That demonstrated the specificity of the assay.

EXAMPLE 4

Intra-Alu Yb8 Assay of Human DNA

Sample #1 of Example 1 was subjected to the procedure of Example 1, using Intra-Alu Yb8 based PCR in place of the Inter-Alu material used in Example 1. Under this approach, it was to be anticipated that the generation of a PCR product would occur only from samples that contained human DNA and that no PCR products would be generated from the samples that contained other DNA sources. The reason is that the recently integrated Alu elements are restricted to the human genome. The anticipated result was the result of the assay.

EXAMPLE 5

Intra-Alu Yb8 Assay of Human/Primate DNA

Sample #2 of Example 2 was subjected to the procedure of Example 4, using Intra-Alu Yb8 amplification in place of the Inter-Alu based PCR amplification used in Example 2. In this assay, templates derived from human DNA, templates with only chimpanzee DNA (a non-human primate), and templates that were mixed and contained human and non-human primate DNA were subjected to amplification. Using these templates, only samples that contained human DNA generated PCR products. Samples that contained only non-human primate DNA did not amplify, thereby indicating the specificity of the assay.

EXAMPLE 6

Intra-Alu Yb8 Assay of Human/Mammal DNA

Sample #3 of Example 3 was subjected to the procedure of Example 4, using Intra-Alu Yb8 PCR in place of the Inter-Alu PCR. In this approach DNA from a human and several other mammals (e.g. cow, sheep, pig) were subjected to amplification either individually or mixed together. Only samples that contained human DNA generated PCR products in the assay. Samples that contained only the DNA of non-human mammals (cow, sheep, pig etc.) did not amplify in the assay, thereby demonstrating that the assay is specific for human DNA.

EXAMPLE 7

Intra-Alu Yd6 Assay of Human DNA

Sample #1 of Example 1 was subjected to the procedure of Example 1, using Intra-Alu Yd6 amplification in place of the Inter-Alu based PCR amplification used in Example 2. In this assay, templates derived from human DNA, templates with only chimpanzee DNA (a non-human primate), and templates that were mixed and contained human and non-human primate DNA were subjected to amplification. Using these templates, only samples that contained human DNA generated PCR products. Samples that contained only non-human primate DNA did not amplify, thereby indicating the specificity of the assay.

EXAMPLE 8

Intra-Alu Yd6 Assay of Human/Mammal DNA

Sample #2 of Example 2 was subjected to the procedure of Example 2, using Intra-Alu Yd6 PCR in place of the Inter-Alu PCR. In this approach, DNA from a human and several other mammals (e.g. cow, sheep, pig) were subjected to amplification either individually or mixed together. Only samples that contained human DNA generated PCR products in the assay. Samples that contained only the DNA of non-human mammals (cow, sheep, pig etc.) did not amplify in the assay, thereby demonstrating that the assay is specific for human DNA.

EXAMPLE 9

Intra-Alu Yd6 Assay of Human/Animal DNA

Sample #3 of Example 3 was subjected to the procedure of Example 3, using Intra-Alu Yd6 PCR in place of the Inter-Alu PCR. In this approach, DNA from a human and several other mammals (e.g. cow, sheep, pig, chicken) were subjected to amplification either individually or mixed together. Only samples that contained human DNA generated PCR products in the assay. Samples that contained only the DNA of non-human mammals (cow, sheep, pig, chicken etc.) did not amplify in the assay, thereby demonstrating that the assay is specific for human DNA.

Figure 3A:
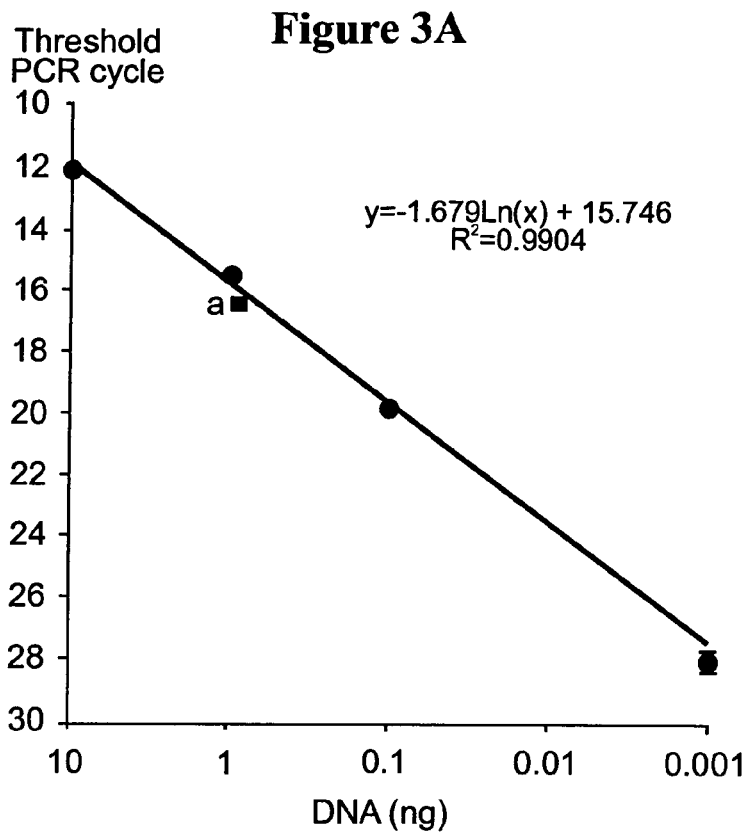
FIGS. 3A through 3C show effective quantitation ranges of various Alu based assays.
Figure 3B:
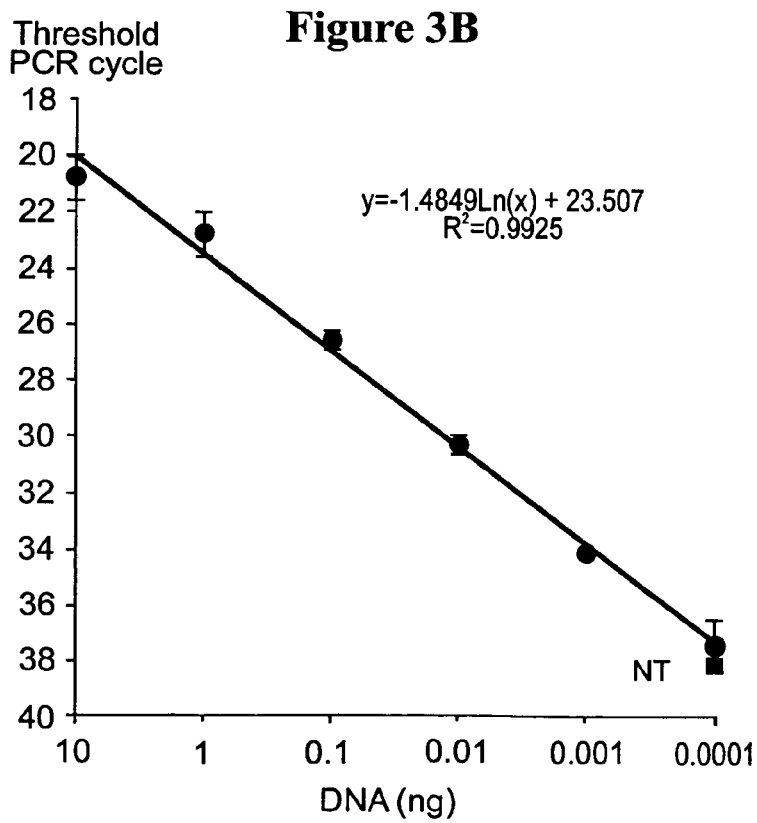
Figure 3C:
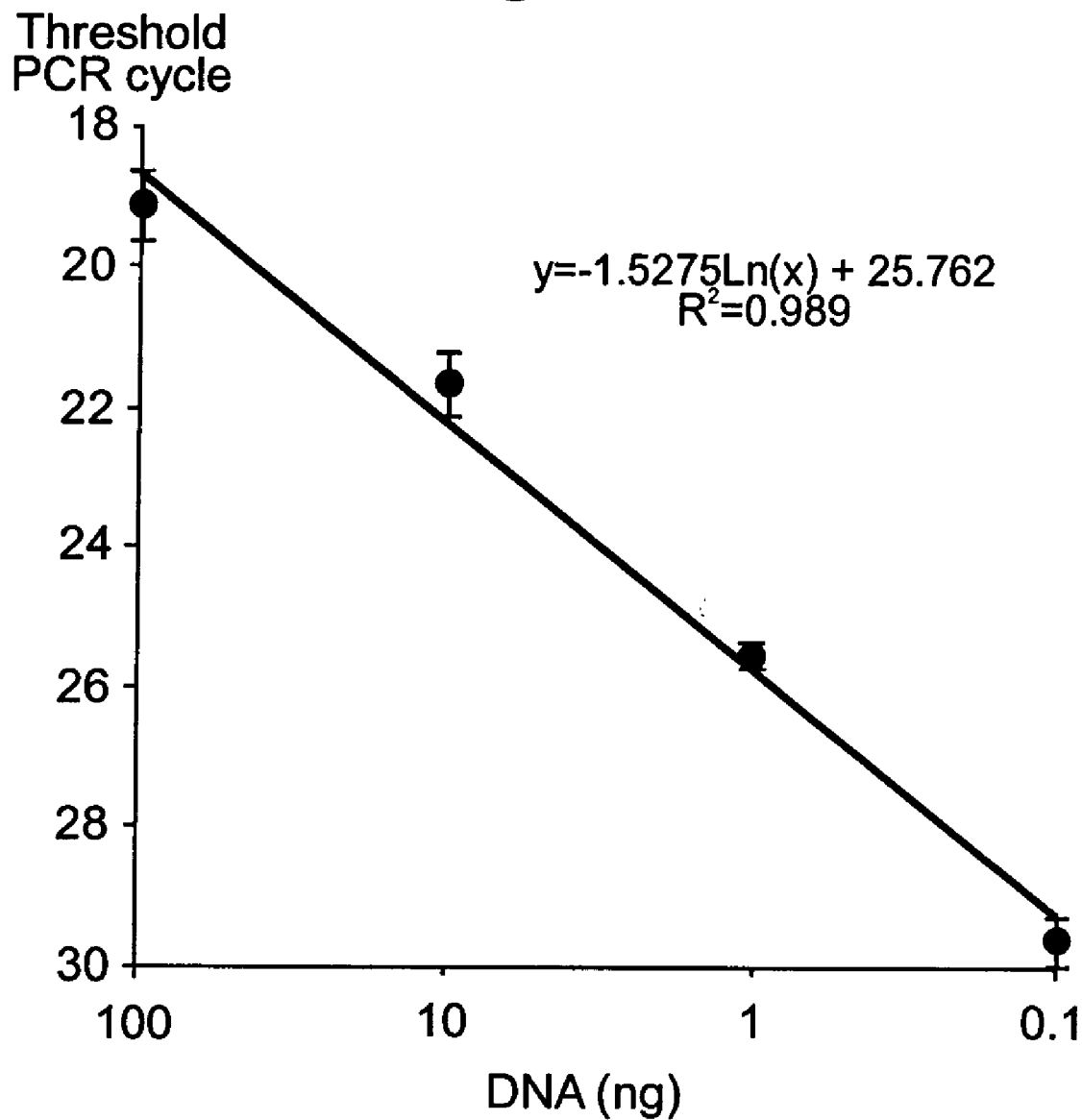

FIG. 3 shows the effective quantitation ranges of various Alu PCR based assays using SYBR green fluorescence detection. FIG. 3A depicts the effective range for Inter-Alu PCR. FIG. 3B depicts the effective range for Intra-Alu Yb8. PCR FIG. 3C depicts the effective range for Intra-Alu Yd6 PCR. The PCR cycle at which the fluorescent signal crosses baseline is considered to be the threshold cycle, plotted on the Y-axis. The fluorescent signal produced by a 10-fold dilution series of human DNA is plotted as the mean of 2-4 replicates, +/− one standard deviation. The $R^2$ value is at least 99% for all three standard curves.

Figure 4A:
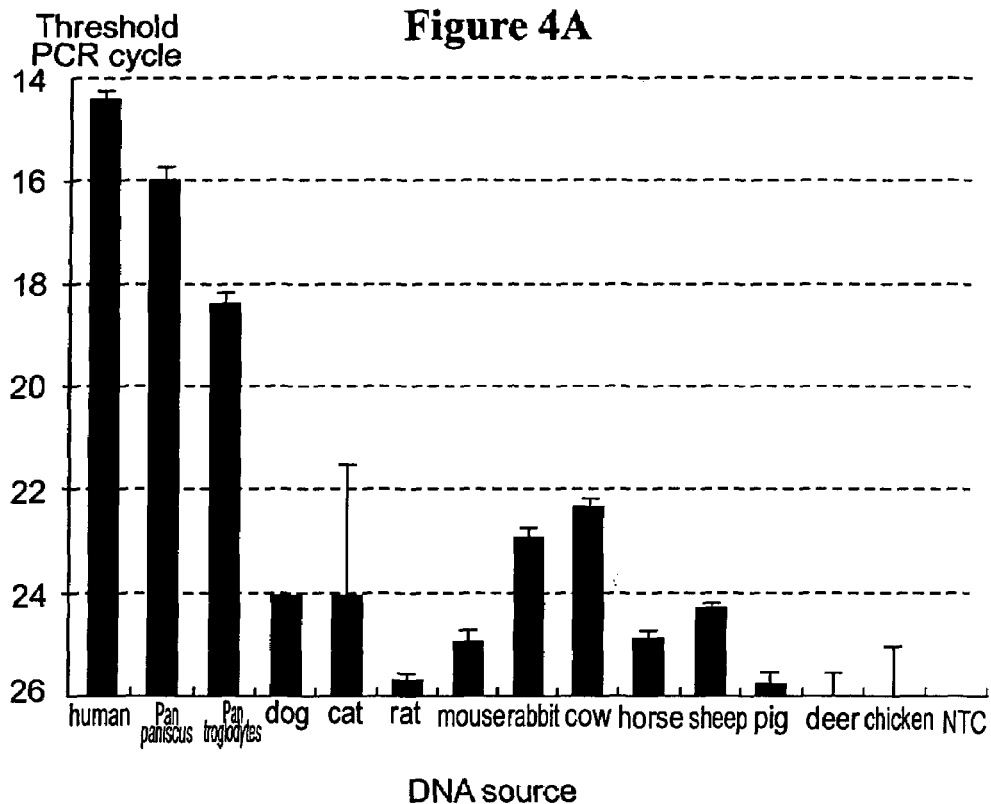
Figure 4B:
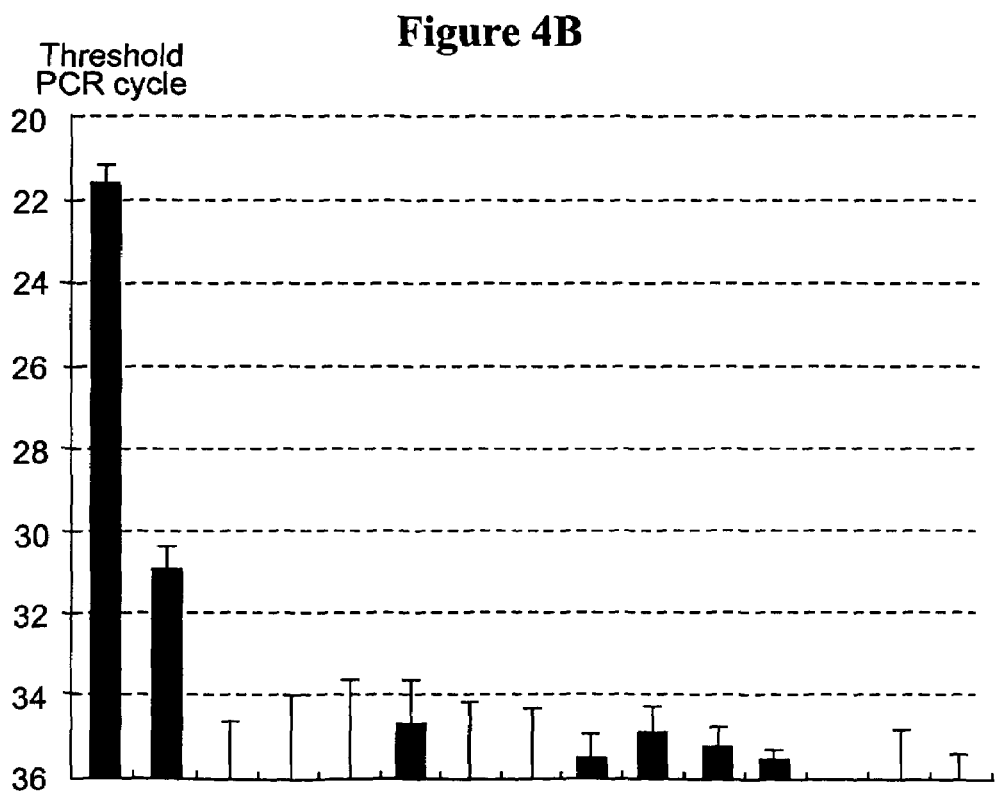

Referring now to FIG. 4, showing background amplification using non-human DNA templates, it is seen that substantially greater cross-amplification exists for inter-Alu PCR based assays using SYBR green fluorescence detection relative to the subfamily-specific intra-Alu assays. FIG. 4 shows the cross amplification of non-human template DNA for inter-Alu (FIG. 4A); intra-Alu Yb8 (FIG. 4B); and intra-Alu Yd6 (FIG. 4C). The PCR cycle at which the fluorescent signal crosses baseline is considered to be the threshold cycle, plotted on the Y-axis (mean of three replicates, +/− one standard deviation).

The inter-Alu assay detected human, pygmy chimpanzee (*Pan paniscus*), and common chimpanzee (*Pan troglodytes*) DNA (2 ng per reaction), but also produced some background amplification using DNA from other mammals as template. The intra-Alu Yb8 assay (2 ng DNA per reaction) and the intra-Alu Yd6 assay (10 ng DNA per reaction) are entirely human-specific with essentially no background amplification using pygmy chimpanzee (the non-human primate thought to be the closest genetic relative to humans) DNA as a template after 30 cycles of PCR.

The inter-Alu based PCR assays had a linear quantitation range of 10 ng to 0.001 ng as shown by the standard curve (FIG. 3A). The mean value of the negative control was 31.3 with a 0.4 standard deviation. This assay was expected to amplify DNA from non-human primates (*Pan paniscus* and *Pan troglodytes*) as well as human DNA. However significant background amplification was also detected in other species when tested with an equivalent amount (2 ng) of non-human DNA (see FIG. 4A). This limits the effective minimum threshold quantitation level of this inter-Alu PCR based assay to 0.01 ng (threshold PCR cycle 22) rather than 0.001 ng, and restricts the range of the inter-Alu based PCR assay to 1000-fold when testing DNA samples from complex sources. To further evaluate the potential background amplification that non-human DNA might have on the assay with respect to human DNA quantitation, an artificial "domestic DNA mix" (10 ng/ml) was prepared that contained 45% canine, 45% feline, and 10% human DNA. The results of that experiment (mean of duplicates, +/− one standard deviation) are shown as data point "a" in FIG. 3A. Since 10% of 10 ng is 1 ng, the assay was able to accurately quantitate the human DNA in the mixed sample.

The intra-Yb8 based PCR assay had a low-scale linear quantitation range of 10 ng to 0.001 ng (10,000-fold) as shown by the standard curve (see FIG. 3B). The value of the no template (NT) negative control was not significantly different than the last data point (0.0001 ng). Background amplification was detected in *Pan paniscus* (pygmy chimpanzee), the most closely related non-human primate, following 31 cycles of PCR and was detected in other species in trace amounts following 36 cycles of PCR using an equivalent amount of DNA template (2 ng) (see FIG. 4B). This demonstrates that the intra-Yb8 assay is human specific to 0.01 ng, and specific to only human and pygmy chimpanzee to 0.001 ng (1 pg) when evaluating mixed DNA samples. If a sample is known to consist of only human DNA, the detection limit of this assay may extend between 1 pg and 0.1 pg but must accompany an appropriate no template control.

The intra-Yd6 based PCR assay had a high-scale linear quantitation range of 100 ng to 0.1 ng (1000-fold) as shown by the standard curve (see FIG. 3C). The mean value of the negative control was 35.7 with a 1.17 standard deviation. No signal was detected from any of the non-human species tested, making this assay absolutely human specific within its quantitation range (see FIG. 4C). The intra-Yd6 assay not only extends the linear quantitative range of the intra-Alu assays combined, it also allows for human DNA detection and rough quantitative estimates to be performed by simple, inexpensive agarose gel electrophoresis as an initial screening tool (see FIG. 5). The quantitation of the human DNA in the mixture sample can be achieved by comparing the intensity of the signal on an agarose gel stained with ethidium bromide from unknown samples with the intensity of standard human DNA or from the calibration curve, which can be generated from the results for the standard human DNA samples.

Figure 5:
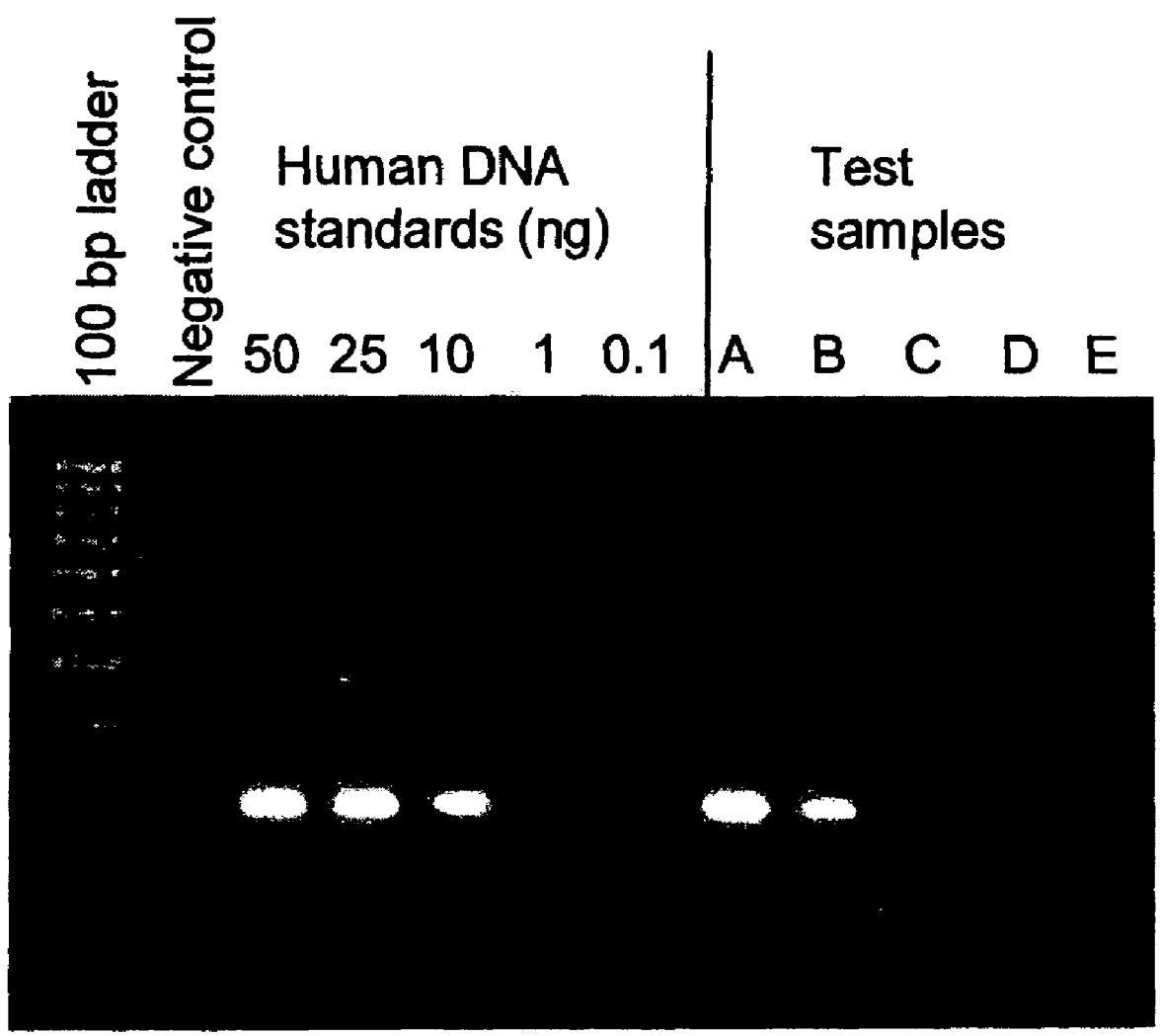
FIG. 5 illustrates human DNA detection on an agarose gel using an intra-Yd6 Alu PCR assay.

FIG. 5 illustrates human DNA detection on an agarose gel using the intra-Yd6 Alu PCR assay. Following 30 cycles of conventional PCR using the intra-Yd6 oligonucleotide primers, amplicons were chromatographed on a 2% agarose gel stained with ethidium bromide. Using the human DNA standards on the left, samples A through C were positive for the presence of human DNA (i.e., they generated a PCR amplicon) while samples D and E were not positive (10 ng chimpanzee or rat DNA template, respectively). Samples A-C contain 30, 5, and 0.5 ng of human DNA, respectively. These values are reasonably consistent with expected values based on empirical observations of fragment intensity. This demonstrates that the assay is a simple, rapid, and inexpensive means of human DNA detection that also provides quantitative estimates of human template DNA.

SUMMARY OF RESULTS

The vast majority of human forensic casework involves the analysis of nuclear loci making the quantitation of human nuclear DNA a paramount issue. There are several advantages to the Alu-based methods disclosed herein for the rapid identification and quantitation of human DNA over commercially available systems and other recently reported methods. First, these assays can use a polymerase chain reaction. If an ample amount of DNA is available for testing, human-specific DNA detection and quantitative estimates can be performed by simple agarose gel analysis using the intra-Yd6 Alu based PCR assay as an initial screening tool. The addition of SYBR green PCR core reagents to the amplification protocol allows accurate quantitation using any qPCR system. No additional special expertise or unique (or expensive) equipment, such as a luminometer or automated DNA sequencer/genotyper is required. This format alone minimizes the cost of performing these analyses on a large-scale and gives most forensic laboratories with average resources the ability to perform these assays.

The inventors have also systematically tested each assay for human specificity, especially with regard to closely related non-human primates and in multiple diverse human genomes. In contrast, documentation associated with other currently available methods is vague with respect to the cross-hybridization/amplification of other closely related species. In addition, the range of quantitation using the combined intra-Alu based assays (Yb8 and Yd6 subfamilies) is approximately $10^5$ based on the above described 10-fold dilution series experiments. By contrast, the current commercial quantitation systems such as AluQuant® and Quantiblot® have a 500-fold and 100-fold quantitation range, respectively. In other words, the low range detection limit of the intra-Yb8 assay described here exceeds the commercial systems by a minimum of 100-fold and it also exceeds the method recently reported by Sifis et al., supra, by at least 2.5-fold. Further, since Sifis et al., supra, do not address possible mammalian cross-amplification with their assay, the intra-Yb8 method reported here is even more sensitive for the identification of human DNA from complex sources.

The high copy number of Alu repeats in the human genome makes these assays ideal for human DNA detection and quantitation. When inter-Alu PCR was first developed over 15 years ago, it was revolutionary in allowing sensitive amplification and detection of human DNA from somatic cell hybrids while circumventing the laborious task of first creating a recombinant library. The detection limit reported then of 0.001 ng of human DNA is consistent with the findings described hereinabove. However, the fact that the present inter-Alu PCR method amplifies unique genomic DNA sequences between adjacent Alu repeats, creating a complex pool of various sized PCR amplicons, makes that method vulnerable to greater cross-amplification potential with DNA from other mammals compared to the intra-Alu methods of the instant invention. Furthermore, the inter-Alu PCR method requires the use of fluorescence or radioactive isotope in the PCR reaction to be quantitative, whereas the intra-Alu methods are more amenable to additional detection schemes such as ethidium bromide or TaqMan® chemistry.

In practicing the instant invention, several caveats are in order. The inventors have observed that the high $T_m$ of the intra-Yb8 Alu based primers is essential to the elimination of artifact amplicons from DNA of other species as a result of sequence similarity to SINE elements from other species. This was manifested when the inventors attempted to design a similar intra-Alu PCR assay using the Ya5 subfamily consensus sequence, but were unable eliminate background amplification. Optimization of oligonucleotide primer concentration also proved to be an important component in the development of these Alu based PCR assays. Compared to single copy PCR reactions, the high number of target sequences in these assays made it important to have sufficient amounts of primer without compromising PCR amplification efficiency.

Kits

It is considered that the scope of the invention extends to kits used to practice the assays of the invention. Thus, it is contemplated that the invention would be exploited by marketing kits for DNA quantitation of unknown biological samples, using the principles and procedures described hereinabove. For example, a DNA quantitation kit comprises a reagent mix and a DNA control. The control contains a predetermined amount of human DNA suspended in an appropriate salt solution. The reagent mix, often termed as Primer Mix, contains the primers, salts, and other chemicals such as dNTPs, in proportions suitable to obtain the desired results. The following examples illustrate representative kits for practicing embodiments of the invention.

EXAMPLE 10

Kit for Quantitating DNA

A kit suitable for performing quantitating DNA includes the primers and polymerase and buffers for the PCR reaction. If the quantitation of DNA by using the above procedure is used at a crime scene, the kit can optionally include the reagents for extracting and isolating DNA from evidence.

For example, the kit includes PCR tubes, sterile water, sterile TLE, SYBR® Green core reagent kit and Human DNA controls, and a pair of primers (e.g., (1) Alu 3-5'GATCGCGCCACTGCACTCC 3' (SEQ ID NO: 1) and Alu 5-5' GGATTACAGGCGTGAGCCAC 3' (SEQ ID NO: 2), (2) 5' CGAGGCGGGTGGATCATGAGGT 3' (SEQ ID NO: 3) (position 48 to 69) and 5' TCTGTCGCCCAGGCCGACT 3' (SEQ ID NO: 4) (position 273 to 254), or (3) 5' GAGATCGAGACCACGGTGAAA 3' (SEQ ID NO: 5) and 5' TTTGAGACGGAGTCTCGTT 3'(SEQ ID NO: 6)).

The concentrations of each reagent can be properly selected depending on the intended use of the kit.

The following examples illustrate the use of the foregoing kits to perform assays in accordance with the invention.

EXAMPLE 11

Procedure for Intro-Alu Yb8 Assay

Human DNA standards (HeLa or other known control) were prepared in steril TLE to 10 ng/µl and serially diluted 10-fold with TLE. Unknown DNA samples in TLE were prepared as was done with the standards. As with any quantitative assay, optimal quantitation occurs in the middle of the linear range of the standard curve. Therefore, it may be useful to analyze more than one concentration of an unknown DNA sample. Stock primers were reconstituted in sterile TLE to a concentration of 100 µM. Then, 0.5 ml of working solution of each primer at 10 µM was made by diluting 50 µl of each stock with 450 µl of TLE. This represents a 10× working concentration of each primer for the intra-Alu Yb8 human DNA quantitative PCR assay. PCR tubes, strips or plate as needed were prepared, and a template showing the location of the negative control (TLE), the positive controls (A 10-fold serial dilution of human control DNA from 10 ng/µl), and each unknown DNA sample to be quantified was made. 1 µl of DNA template was pipetted into each appropriate well. Then a master mix of all remaining PCR reagents as shown in Table 1 was prepared. 49 µl of master mix was pipetted into each well to make a final PCR reaction volume of 50 µl, as recommended by the manufacturer (SYBR® Green PCR core reagent kit). PCR tubes or plate is placed into the Z-PCR machine. The PCR was performed by subjecting to an initial denaturation of 12 minutes at 95° C., followed by 40 amplification cycles of 95° C. for 15 seconds and 61° C. for 1 minute to anneal and extend. The amplification experiments were performed using an ABI prism 7,000 sequence detection system (Applied Biosystems, Inc.) or a Bio-Rad i-cycler iQ real-time PCR detection system. A calibration curve was generated from the results for the standard DNA samples. The quantity of the human DNA in the unknown sample was computed from the calibration curve.

TABLE 1

| OPCR reagents | Final conc. | volume (µl) | example for 32 |
|---|---|---|---|
| Sterile Water | | 23.75 | 760 |
| SYBR ® Green PCR Buffer (10X)* | 1X | 5 | 160 |
| Intra-Alu Yb8-Forward (10 µM; 10X) | 1 µM | 5 | 160 |
| Intra-Alu Yb8-Reverse (10 µM; 10X) | 1 µM | 5 | 160 |
| dNTPs (12.5 mM)* | 1 mM | 4 | 128 |
| MgCl2 (25 mM)* | 3 mM | 6 | 192 |
| AmpliTaq Gold (5 Unit/ul)* | 1.25 Units | 0.25 | 8 |
| Total: (49 µl X 32) | | 49 µl | 1568 |

*Provided in the SYVR green PCR reagent core kit (ABI part number 4304886)

Several alternative methods for human DNA detection, and quantitation, inter-Alu and intra-Alu based PCR, have been described above. Although the original inter-Alu PCR method revolutionized human DNA detection when it was first developed, the instant disclosure has now demonstrated that the intra-Alu based PCR method is more suited to modern forensic needs. The subfamily-specific intra-Alu assays presented herein, Yb8 and Yd6, employ the amplification of a high copy number of target sequences to achieve very sensitive human-specific DNA detection, while simultaneously maintaining some of the same advantages of a single locus PCR. For example, the amplified products are a uniform size amplicon in each assay, conducive to easy visualization. These amplicons are also short enough (226 bp for Yb8 and 200 bp for Yd6) to tolerate sheered or degraded DNA often associated with forensic applications.

While the invention has been described in connection with specific and preferred embodiments thereof, it is capable of further modifications without departing from the spirit and scope of the invention. This application is intended to cover all variations, uses, or adaptations of the invention, following, in general, the principles of the invention and including such departures from the present disclosure as come within known or customary practice within the art to which the invention pertains, or as are obvious to persons skilled in the art, at the time the departure is made. It should be appreciated that the scope of this invention is not limited to the detailed description of the invention hereinabove, which is intended merely to be illustrative, but rather comprehends the subject matter defined by the following claims.

What is claimed is:

1. A process for quantitating a human DNA in a sample, said process comprising the steps of:
   providing a sample to be analyzed;
   amplifying predetermined genomic DNA of an Alu element subfamily by using primers, said Alu element subfamily being more enriched in the human genome than in any non-human primate genome, the amplification being intra-Alu polymerase chain reaction amplification, each of said primers including a subfamily-specific diagnostic mutation, said Alu element subfamily being Yb8 subfamily or Yd6 subfamily; and
   measuring the amount of the human DNA by comparing the amplified DNA with a reference to quantitate the human DNA in the sample.

2. The process of claim 1, wherein the amplification is a polymerase chain reaction with the primers containing the following sequences:

```
5' CGAGGCGGGTGGATCATGAGGT 3'    (SEQ ID NO: 3)
and

5' TCTGTCGCCCAGGCCGGACT 3'.     (SEQ ID NO: 4)
```

3. The process of claim 1, wherein the amplification is a polymerase chain reaction with the primers containing the following sequences:

```
5' GAGATCGAGACCACGGTGAAA 3'    (SEQ ID NO: 5)
and

5' TTTGAGACGGAGTCTCGTT 3'.     (SEQ ID NO: 6)
```

4. The process of claim 1, wherein the measurement step comprises the step of measuring the amount of the human DNA on an agarose gel stained with ethidium bromide.

5. The process of claim 1, wherein the measurement step comprises the step of measuring the amount of the human DNA by using a qPCR system.

6. The process of claim 1, wherein the measurement step comprises the step of measuring the amount of the human DNA by using TaqMan chemistry.

7. A process for quantitating a human DNA in a sample, said process comprising the steps of:
providing a sample to be analyzed;
amplifying predetermined genomic DNA of an Alu element subfamily by using primers, each of said primers including a subfamily-specific diagnostic mutation, a copy number of said predetermined genomic DNA in the human genome being higher than a copy number of said predetermined genomic DNA in any non-human primate genome, the amplification being intra-Alu polymerase chain reaction amplification, said Alu element subfamily being Yb8 subfamily or Yd6 subfamily; and
measuring the amount of the human DNA by comparing the amplified DNA with a reference.

8. A process for quantitating a human DNA in a sample, said process comprising the steps of:
providing a sample to be analyzed;
amplifying predetermined genomic DNA of an Alu element subfamily by using primers, said Alu element subfamily being Yd6 subfamily, said Alu element subfamily being more enriched in the human genome than in any non-human primate genome, the amplification being intra-Alu polymerase chain reaction amplification; and
measuring the amount of the human DNA by comparing the amplified DNA with a reference to quantitate the human DNA in the sample.

9. A process for quantitating a human DNA in a sample, said process comprising the steps of:
providing a sample to be analyzed;
amplifying predetermined genomic DNA of an Alu element subfamily by using primers, said Alu element subfamily being Yd6 subfamily, said predetermined genomic DNA including subfamily-specific diagnostic mutations, a copy number of said predetermined genomic DNA in the human genome being higher than a copy number of said predetermined genomic DNA in any non-human primate genome, the amplification being intra-Alu polymerase chain reaction amplification; and
measuring the amount of the human DNA by comparing the amplified DNA with a reference.

* * * * *

SEQUENCE LISTING

<160> NUMBER OF SEQ ID NOS: 9

<210> SEQ ID NO 1
<211> LENGTH: 19
<212> TYPE: DNA
<213> ORGANISM: Artificial
<220> FEATURE:
<223> OTHER INFORMATION: Primer (Alu3) for inter-Alu PCR

<400> SEQUENCE: 1
gatcgcgcca ctgcactcc                                                19

<210> SEQ ID NO 2
<211> LENGTH: 20
<212> TYPE: DNA
<213> ORGANISM: Artificial
<220> FEATURE:
<223> OTHER INFORMATION: Primer (Alu5) for inter-Alu PCR

<400> SEQUENCE: 2
ggattacagg cgtgagccac                                               20

<210> SEQ ID NO 3
<211> LENGTH: 22
<212> TYPE: DNA
<213> ORGANISM: Artificial
<220> FEATURE:
<223> OTHER INFORMATION: The forward intra Yb8 primer for intra-Alu PCR

<400> SEQUENCE: 3
cgaggcgggt ggatcatgag gt                                            22

<210> SEQ ID NO 4
<211> LENGTH: 20
<212> TYPE: DNA
<213> ORGANISM: Artificial
<220> FEATURE:
<223> OTHER INFORMATION: The reverse intra Yb8 primer for intra-Alu PCR

<400> SEQUENCE: 4
tctgtcgccc aggccggact                                               20

<210> SEQ ID NO 5
<211> LENGTH: 21
<212> TYPE: DNA
<213> ORGANISM: Artificial
<220> FEATURE:
<223> OTHER INFORMATION: The forward intra Yd6 primer for intra-Alu PCR

<400> SEQUENCE: 5
gagatcgaga ccacggtgaa a                                             21

<210> SEQ ID NO 6
<211> LENGTH: 19
<212> TYPE: DNA
<213> ORGANISM: Artificial
<220> FEATURE:
<223> OTHER INFORMATION: The reverse intra Yd6 primer for intra-Alu PCR

```
<400> SEQUENCE: 6
tttgagacgg agtctcgtt                                              19

<210> SEQ ID NO 7
<211> LENGTH: 287
<212> TYPE: DNA
<213> ORGANISM: Homo sapiens

<400> SEQUENCE: 7
cgccgggcgc ggtggcgcac gcctgtaatc ccagcacttt gggaggccga ggcgggcgga    60
tcacgaggtc aggagatcga gaccatcctg gctaacacgg tgaaacccccg tctctactaa  120 aaatacaaaa aattagccgg gcgtggtggc gggcgcctgt agtcccagct actcgggagg   180
ctgaggcagg agaatggcgt gaacccggga ggcggagctt gcagtgagcc gagatcgcgc   240
cactgcactc cagcctgggc gacagagcga gactccgtct caaaaaa                287

<210> SEQ ID NO 8
<211> LENGTH: 294
<212> TYPE: DNA
<213> ORGANISM: Homo sapiens

<400> SEQUENCE: 8
cgccgggcgc ggtggcgcac gcctgtaatc ccagcacttt gggaggccga ggcgggtgga    60
tcatgaggtc aggagatcga gaccatcctg gctaacaagg tgaaacccccg tctctactaa  120 aaatacaaaa aattagccgg gcgcggtggc gggcgcctgt agtcccagct actcgggagg   180
ctgaggcagg agaatggcgt gaacccggga agcggagctt gcagtgagcc gagattgcgc   240
cactgcagtc cgcagtccgg cctgggcgac agagcgagac tccgtctcaa aaaa         294

<210> SEQ ID NO 9
<211> LENGTH: 275
<212> TYPE: DNA
<213> ORGANISM: Homo sapiens

<400> SEQUENCE: 9
cgccgggcgc ggtggcgcac gcctgtaatc ccagcacttt gggaggccga ggcgggcgga    60
tcacgaggtc aggagatcga gaccacggtg aaacccccgtc tctactaaaa atacaaaaaa 120
ttagccgggc gcagtggcgg gcgcctgtag tcccagctac tcgggaggct gaggcaggag  180
aatggcgtga acccggaagg cggagcttgc agtgagcgga gatcgcgcca cagcactccc   240
gcctgggcga cagaacgaga ctccgtctca aaaaa                             275
```